United States Patent [19]

Harm et al.

[11] Patent Number: 4,650,766

[45] Date of Patent: Mar. 17, 1987

[54] CULTURING APPARATUS

[75] Inventors: William H. Harm, Columbia Heights; John J. Peluso, Coon Rapids, both of Minn.

[73] Assignee: Endotronics, Inc., Coon Rapids, Minn.

[21] Appl. No.: 658,548

[22] Filed: Oct. 9, 1984

[51] Int. Cl.⁴ ............................................. C12M 3/00
[52] U.S. Cl. .................................. 435/284; 435/289; 435/313
[58] Field of Search ................ 435/284, 289, 313, 290

[56] References Cited

U.S. PATENT DOCUMENTS 3,218,758 11/1965 Konikoff ........................ 435/313 X
3,241,943 3/1986 Bystrom ......................... 435/313 X Primary Examiner—Alan Cohan
Attorney, Agent, or Firm—Kinney & Lange

[57] ABSTRACT

An apparatus for growing and maintaining microorganisms or cells within a culturing chamber simultaneously heats and gasses a nutrient solution being delivered through the culturing chamber. The apparatus includes a pump for pumping the nutrient solution from a nutrient source through gas-diffusable tubing to a heating and gassing block. From the heating and gassing block, the nutrient solution is transported through the tubing to the culturing chamber. A heating source preferably delivers water at a predetermined temperature to fluid passages of a retention well in which the culturing chamber is maintained, and through the heating and gassing block such that the retention well and the heating and gassing block are kept essentially at the same temperature. Gas from a gas source is presented to the tubing through the heating and gassing block for diffusion through the tubing into the nutrient solution.

15 Claims, 7 Drawing Figures

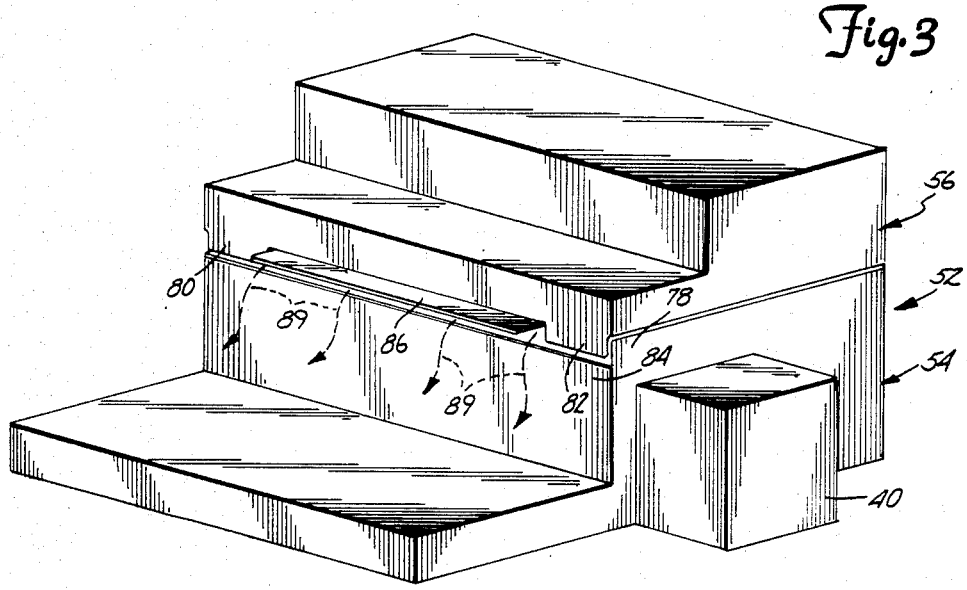
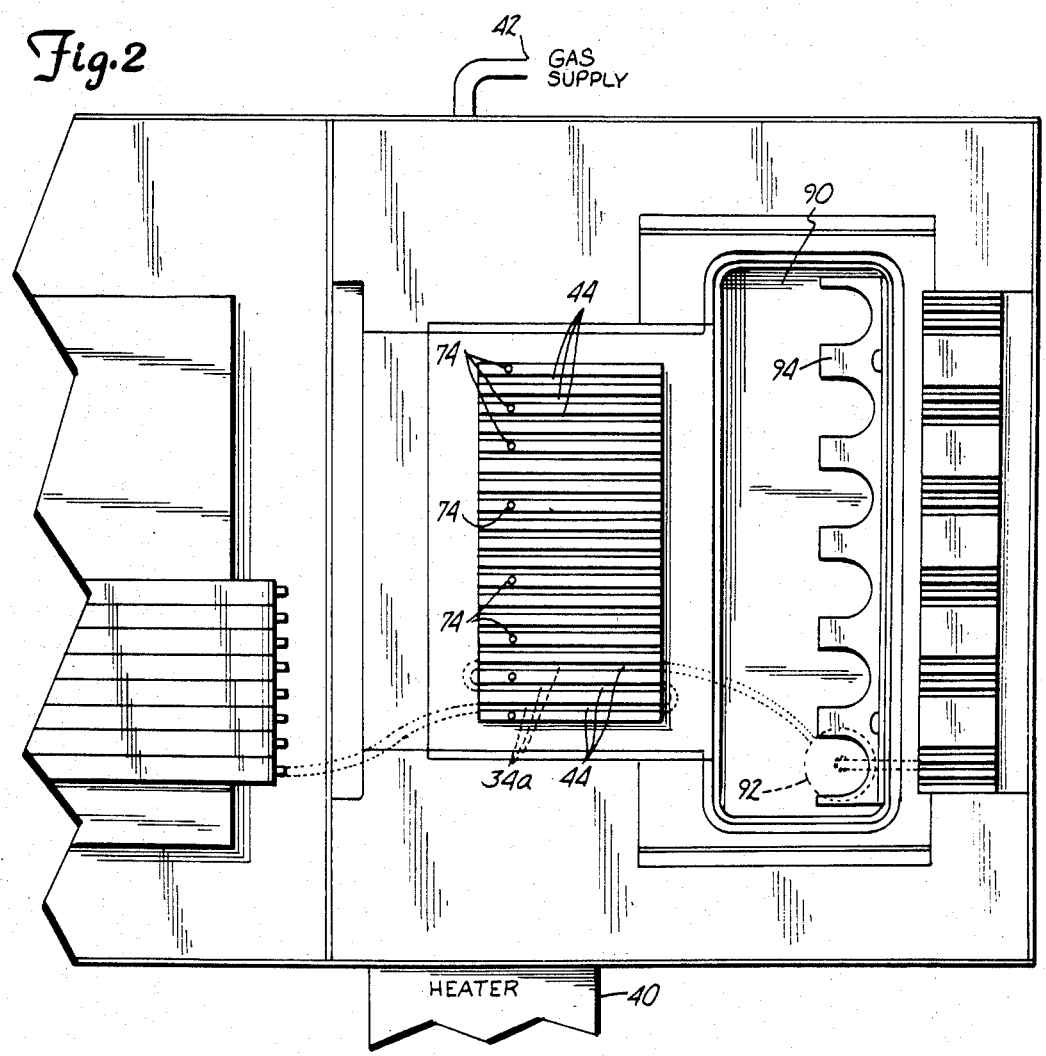

CULTURING APPARATUS

BACKGROUND OF THE INVENTION

1. Field of the Invention.

The present invention relates to an apparatus for the growth and maintenance of microorganisms or cells in culture.

2. Description of the Prior Art.

In order to grow microorganisms or cells in vitro, the environment in which the cells or microorganisms are maintained must be very carefully controlled. Variables, such as nutrients, gasses, and temperature must be maintained at the proper level for the cells or microorganisms to grow in an optimal manner. A nutrient solution containing $CO_2$ and/or $O_2$ is pumped into a culturing chamber in which the cells or microorganisms are held. The $CO_2$ and/or $O_2$ is used to control the pH of the nutrient solution and permit the cell or microorganism to properly respirate.

One prior art method of introducing $CO_2$ and/or $O_2$ into the nutrient solution is to gas the nutrient solution in its source container. Either the head-space in the source container is gassed or the nutrient solution is bubbled. Bubbling of the nutrient solution, however, tends to cause proteins to combine into larger aggregations which may change the fluid and biochemical properties of the nutrient solution. The nutrient solution is then delivered through silicone tubing to the culturing chamber. A pump is typically positioned between the nutrient source and the culturing chamber to provide the motive force to deliver the nutrient solution to the chamber. The silicone tubing is gas-diffusable and is well known, and since the distance from the source container to the culture chamber is relatively long and the flow rate relatively slow, much of the gas within the nutrient solution diffuses out of the silicone tubing.

Another method of introducing $CO_2$ and/or $O_2$ into the nutrient solution is to introduce gas directly into the culture chamber. The culture chamber is only partially filled with the nutrient solution, creating a head-space within the chamber. The head-space is then directly filled with gas. Vessel geometry is consequently critical because of the need to maintain an optimum surface area to total liquid volume ratio. In addition, agitation is also critical since the surface liquid must be circulated downward while the liquid at the bottom of the chamber must be brought to the surface (or at least into contact with highly gassed surface liquid) in order for the nutrient solution to be gassed properly. However, adverse conditions such as overgassing and cell damage due to surface tension and osmotic gradients occur at or proximate the air/liquid interface and mechanical agitation of the culture chamber may produce cell damage.

Microorganisms and cells are maintained at a predetermined temperature for growth. The culturing chamber is commonly kept in a water bath or air incubator which is held at a constant temperature. To avoid thermally shocking the microorganisms or cells with a nutrient solution having a temperature different than the culturing chamber, the incoming nutrient solution is typically prewarmed by passing it through a length of tubing (silicone) which is submerged in the same water bath as the chamber. This method, however, is difficult to use when sterility must be maintained or a sterile culture recovery is required. Furthermore, the silicone tubing acts as a membrane through which some ion transfer may occur. The ion transfer results in uncontrolled modification of the chemistry of the nutrient solution.

Another method that has been used to heat and gas the nutrient solution includes using a gassed incubator that may include a static culture, or a batch exchange culture, or a perifusion system with pumps, tubing and culture chambers within the incubator. This method, although eliminating many of the problems of the water bath described above, requires a relatively large amount of space, especially when using a perifusion system.

Other attempts have been made to heat the nutrient solution through the use of electric heaters. However, a significant amount of heat loss occurs through the tubing and creates a problem in trying to keep the temperature of the incoming nutrient solution the same as the temperature in the culture chamber. In addition, sophisticated controller systems that attempt to monitor both the culture chamber and the warmed nutrient solution and control the temperature of the incoming nutrient solution are costly, complex, require constant calibration, and are generally ill suited to the small volumes and low flow rates used in most tissue culture systems.

SUMMARY OF THE INVENTION

The present invention includes an apparatus for growing and maintaining organisms or cells within a culturing device. The apparatus includes a retention well for maintaining the culturing device at a predetermined temperature, a heating and gassing block that simultaneously heats and gasses the nutrient solution, and a pumping section for pumping the nutrient solution from a source through gas-diffusable tubing. The tubing extends through the heating and gassing block and is fluidly connected to the culturing device in the retention well. An energy source provides energy, preferably using a heated fluid such as water, to the retention well and to the heating and gas block such that the nutrient solution and the culturing device in the retention well are maintained at substantially the same temperature using the same heating source. The heating and gassing also receives gas from a gas source and presents the gas to the tubing for diffusion into the nutrient solution.

BRIEF DESCRIPTION OF THE DRAWINGS

FIG. 2 is an enlarged top view with a cover off of a portion of the apparatus base illustrating a heating block and a culturing device retention well.

FIG. 3 is a perspective view of the present invention without a pumping section.

DETAILED DESCRIPTION OF THE PREFERRED EMBODIMENTS

Figure 1:
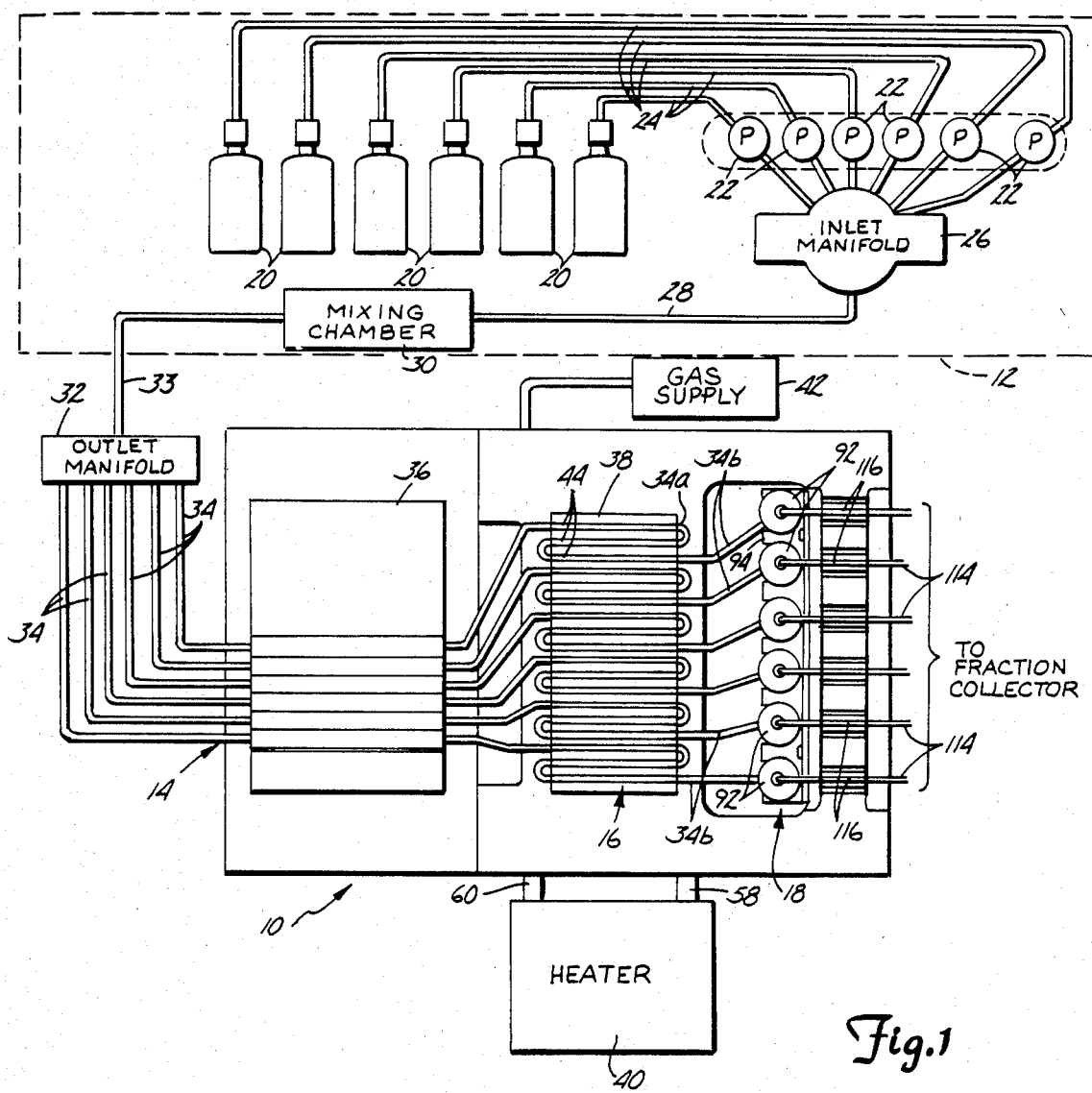
FIG. 1 is a schematic view of the apparatus of the present invention including the nutrient source.

An apparatus 10 of the present invention is schematically illustrated in FIG. 1. The apparatus 10 includes a nutrient supply source 12, a multiple channel pumping section 14, a heating and gassing section 16, and a cell culturing section 18.

The nutrient supply source 12 preferably includes a plurality of vessels 20, each vessel 20 containing either a different nutrient or a different concentration of a nutrient or other chemical or combination of both. Each of the vessels 20 is fluidly connected to a respective pump by tubing 24. The pumps 22 are in turn fluidly connected to an inlet manifold 26. From the inlet manifold 26, the nutrient solution is transported through conduit 28 to a mixing chamber 30. The pumps 22 are operated by a control system (not shown) so that nutrient solution from preselected containers 20 is pumped to the inlet manifold and into the mixing chamber under a predetermined administration schedule. Suitable control systems are manufactured by Endotronics, Inc. of Minnesota under the trademark "ACUSYST" and "APS10". The mixing chamber 30 serves as an integration point for the various nutrient solutions and provides an output stream with a known concentration at any particular point in time.

The pumping section 14 includes an output manifold 32 that is fluidly connected by tubing 33 with the mixing chamber 30. From the outlet manifold 32, the nutrient solution is transported in a plurality of separate streams through a plurality of separate sections of tubing 34 which extend through the pumping section 14, through the heating and gassing section 16 and into the cell culturing section 18. The pumping section 14 preferably includes a multi-channel peristaltic pump unit 36. A suitable multi-channel pump unit is sold by Ismatec, SA, Zurich, Switzerland. The multi-channel peristaltic pump provides motive force for delivering the streams of nutrient solution through the heating and gassing section 16 and to the culturing section 18.

The heating and gassing section 16 includes a heating and gassing block 38, a heater 40 for providing energy to the heating and gassing block 38, and a gas supply 42. The heating and gassing section 16 is used to "condition" the nutrient solution just prior to delivery to the culturing section 18. The heating and gassing section brings the nutrient solution to a preselected temperature and adds gas to the nutrient solution.

Preferably, the heating and gassing block 38 is made of a metal, such as aluminum, and includes a plurality of grooves 44 that frictionally retain sections 34a of the tubing 34 in heat transfer relationship, as illustrated in both FIGS. 1 and 2. A sufficient length of each tubing section 34 is in heat transfer relationship with the heating and gassing block 38 so that the desired temperature of the nutrient solution is achieved during the nutrient solution's travel through the heating and gassing block 38. The length of tubing section 34a is determined by calculating for heat transfer and experimentally determining the rate of gas transfer or calculating the rate of gas transfer. The tubing 34 is frictionally retained by engagement of the majority of the surface area of the tubing by a plurality of grooves 44. As much of the circumference as possible is in heat transfer relationship with the heating and gassing block to increase the efficiency of heat transfer. However, the grooves 44 have an opening sufficient for easy removal and replacement of the sections 34a. In one preferred embodiment, each section 34a was retained by three grooves 44 with nutrient solution, in effect, making three passes through the heating and gassing block 38 for heat transfer.

Figure 4:
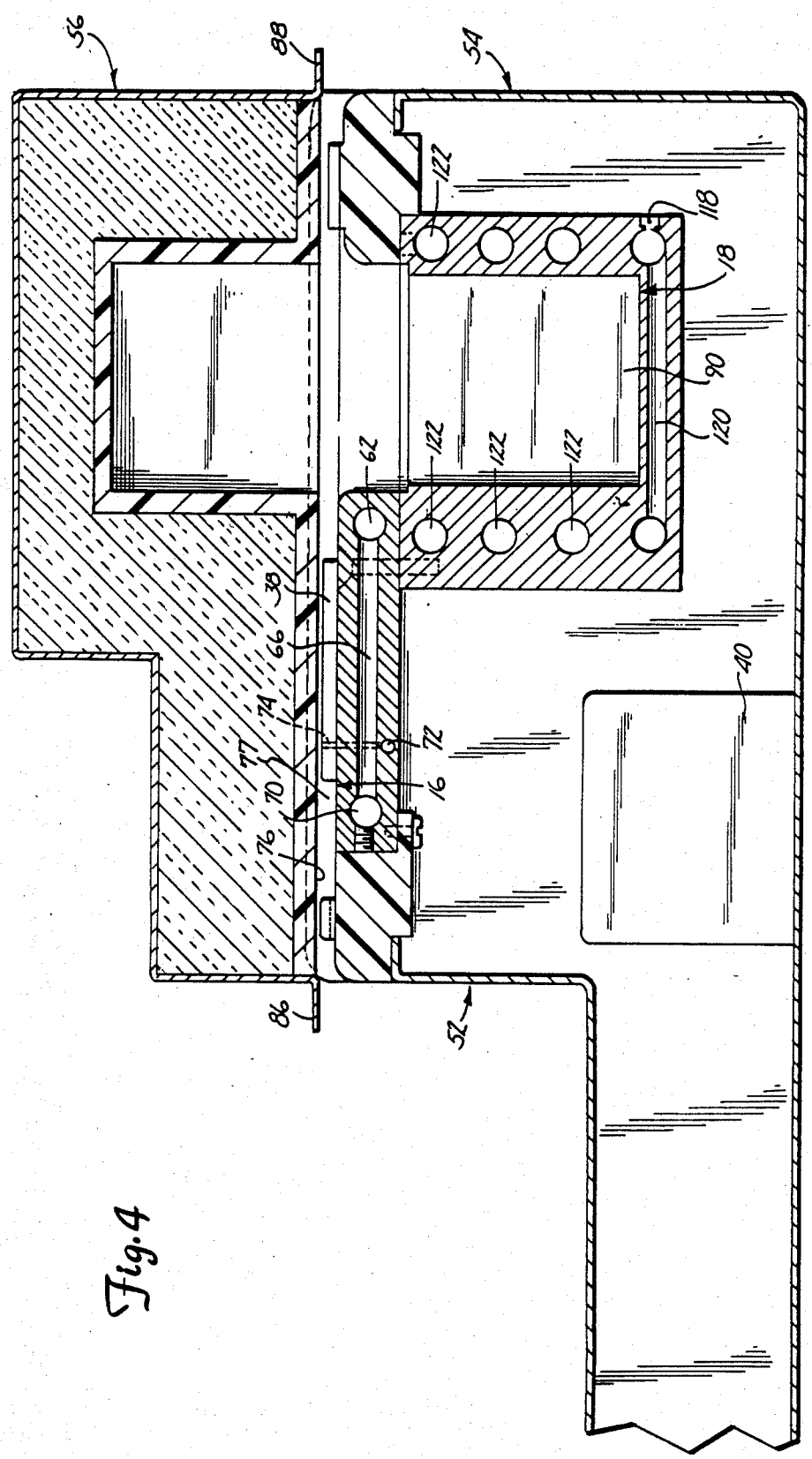
FIG. 4 is a partial sectional view showing the heating and gassing section and the device retention well.

The heating and gassing section 16 and the culturing section 18 are located in a housing 52, illustrated in FIGS. 3 and 4. The housing includes a lower base section 54 and an upper cover 56. The heating and gassing section 16 and the culturing section 18 are specifically located in the base 54.

In one working embodiment, the heater 40 is a hot water heater. The heater 40 can be an internal or an external heater. A suitable external heater is marketed under the trademark of "Precision H5A" by the Precision Marketing Group of Chicago, Ill. The heater 40 is shown outside the housing 52 for illustrative purposes and is preferably located within the base 54. The hot water flows from heater 40 to the base section 54 through conduit 58 and back through conduit 60, as illustrated in FIG. 1. The heated water is preferably initially conveyed into the culturing section 18 and then into the heating and gassing section 16 and returned to the heater 40. Consequently, only one simple heat controller is used to hold the cell culturing section and the incoming nutrient solution at substantially the same temperature.

Figure 5:
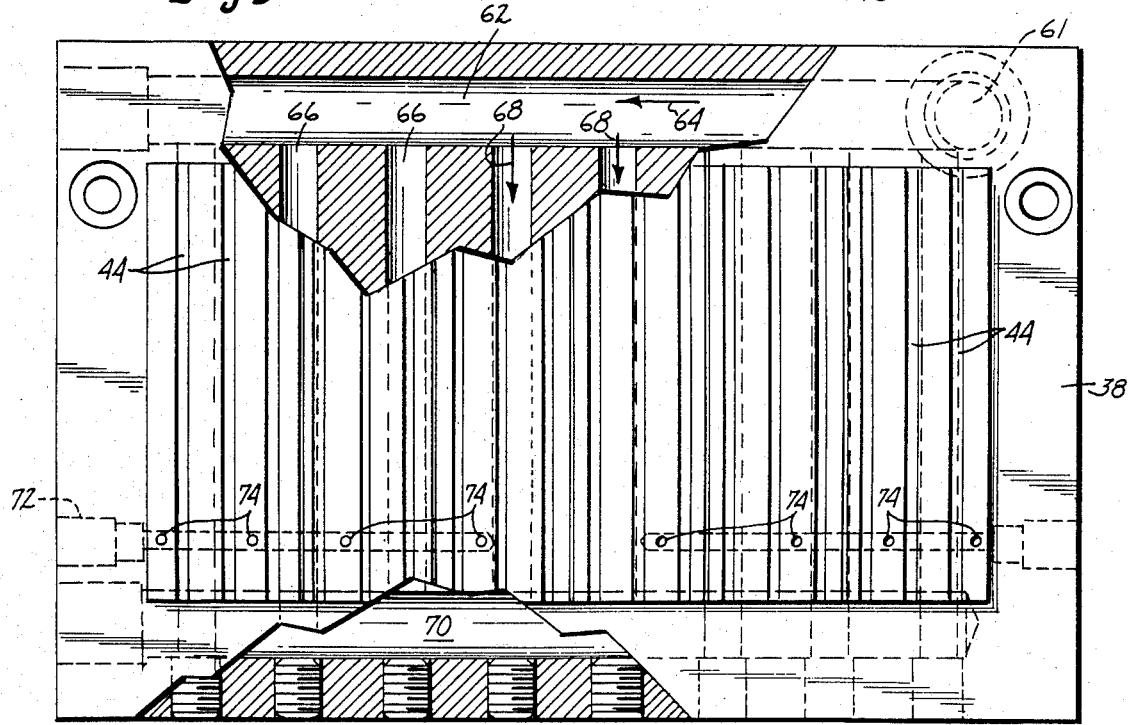
FIG. 5 is a top view of a heating and gassing block with a portion broken away to show fluid and gas passages.

The heated water flows from the culturing section through an opening 61 into an inlet manifold passage 62 that extends across a width of the heating and gassing block 38, as illustrated in FIG. 5. The heated water flows in the general direction of arrow 64 through the manifold passage 62. A plurality of fluid passages 66 in the heating and gassing block 38 are disposed along the same general direction as the grooves 44 and are in fluid communication with the manifold passage 62. Heated water flows from the manifold passage 64 through the passages 66 as indicated by arrows 68 for the even transfer of heat throughout the heating and gassing block 38, for heat absorption by the tubing sections 34a retained in the grooves 44 and for ultimate heat transfer to the nutrient solution.

In the same working embodiment, each of the grooves 44 are approximately 2.9 inches in length and are approximately 0.0781 in width. The passages 66 have approximately a 0.25 diameter and are vertically spaced from the central axis of the passages to the lowermost portion of the grooves 44 approximately 0.205 inches. The close proximity of the passages 66 to the grooves 44 provides for relatively efficient heat transfer through the heating and gassing block.

The passages 66 are fluidly connected to an outlet manifold passage 70 into which the water from the passages 66 flows. From the outlet manifold passage 70, the water flows through the base section 54 and back into the heater 40.

In the heating and gassing section 16, while the nutrient solution is passing through the heating and gassing block, it is also infused with gas. The gas is usually a well known combination of $CO_2$ and oxygen particular to the type of organism being cultured.

The gas from the gas supply 42 is conveyed through passages (not shown) in the base section 54 to a gas manifold passage 72 in the block 38. The gas manifold passage 72 runs generally transverse to the direction of the grooves 44. A plurality of gas delivery passages 74 are connected to the gas manifold passage 72 and extend upwardly therefrom to an upper surface of the heating and gassing block 38.

The cover 56 aids in diffusing the gas through the tubing sections 34a and into the nutrient solution. The cover 56 has a bottom surface 76, illustrated in FIG. 4, that almost comes in contact with the top surface of the heating and gassing block 38 when the cover 56 is in a closed position. In the working embodiment previously mentioned, the distance from the bottom surface 76 to the top surface of the heating and gassing block is approximately 0.050 inches. The base 54 includes a right side lip portion 78 and a like left side lip portion (not shown) which overlaps outer side portions of the cover 56 when the cover is closed. The cover 56 includes front lip portions 80 and 82 which overlap a front wall 84 of the base 54, as illustrated in FIG. 3. Similarly, downwardly extending lip portions (not shown) are included on the back side of the cover 56 that overlap a back wall of the base 54.

The cover 56 also includes an outwardly-extending front lip portion 86 and an outwardly-extending rearward lip portion 88, as illustrated in FIGS. 3 and 4. The outwardly-extending lip portion forms a passage that permits gas flow from the housing 52, as indicated by arrows 89, and permits entry of the tubing from the pumping section to the housing 52 for passage through the heating and gassing block 38. Likewise, the rearward outwardly-extending lip portion 88 permits gas flow from the unit 52 and provides an exit for the tubing from the culturing section 18.

Preferably, the cover 56 is completely removable to permit unencumbered access. When the cover 56 is in a closed position, gasses exiting the heating and gassing block 38 through the passages 74 fill a small volume 77 between the top surface of the heating and gassing block 38 and the lower surface 76 of the cover 56 at a concentration and pressure sufficient to cause diffusion of the gasses through the tubing sections 34a and into the nutrient solution. In the working embodiment previously mentioned, it is believed that the pressure is essentially atmospheric.

The culturing section 18 includes a culturing chamber retention well 90 that is preferably dry and filled with gas held at a constant temperature. In addition, the well 90 can contain a liquid such as water. A plurality of culturing chambers 92 are positioned within the well 90, as illustrated in FIGS. 1 and 2. The culturing chambers 92 are preferably retained in position by a bracket 94 that is attached at the top of the well 90, as illustrated in FIGS. 1 and 2.

Figure 6:
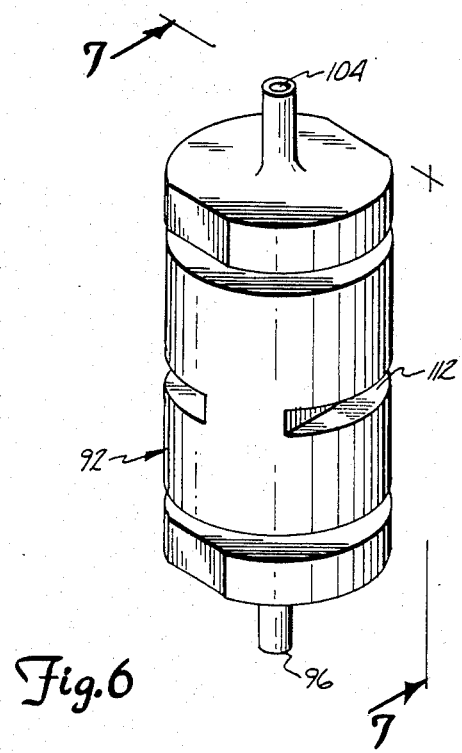
FIG. 6 is a perspective view of a culturing device.
Figure 7:
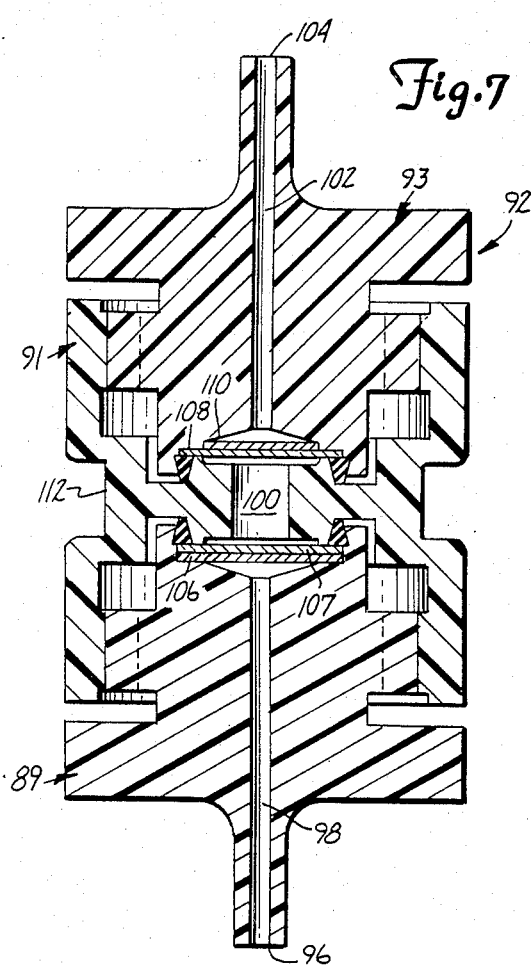
FIG. 7 is a sectional view of the culturing device taken along the line 7—7 of FIG. 5.

The culturing chambers 92 are more fully illustrated in FIGS. 6 and 7. The culturing chamber 92 includes a bottom cap portion 89, a middle portion 91 and a top cap portion 93 that define an inlet 96, an inlet passage 98, an inner chamber 100, an outlet passage 102 and an outlet 104. A lower filter 106 and screen 107 are disposed between the inner chamber 100 and the inlet passage 98 to filter the nutrient solution flowing into the inner chamber and to retain the organism being cultured. In addition, a first upper filter 108 and an optional support screen 110 are disposed between the inner chamber 100 and the outlet passage 102. The screen 110 may be used alone to retain small organs within the chamber or may be used to support the filter 108. The use of both the filter 108 and the screen 110 together depends upon the material of which the filter 108 is made of and the flow rate through the chamber. The inlet filter, 106, may also be used in conjunction with the support screen 107 or may be used with a filter only, screen only or filter and screen. Generally, when a filter is used with a support screen, the screen is placed on the downstream side of the filter.

The main body of the culturing chamber has an exterior central groove 112 that engages the bracket 94, as illustrated in FIGS. 1 and 2, so that the chamber 92 can be held in position within the well 90.

The inlet opening 96 is connected to tubing sections 34b that extend from the heating and gassing block so that nutrient solution can be conveyed into the inner chamber 100, as illustrated in FIG. 1. The tubing sections 34b are integral with 34a and are approximately two and one-half inches (2½") in length with the overall lengths of sections 34a and 34b Dombined being approximately fifteen inches (15"). It should be understood that gassing of the tubing sections 34b also occurs due to the flow of gas from the heating and gassing block 38 towards the rear of the unit. Therefore, the nutrient solution is being gassed up until the point of entry into the culture chambers 92. The outlet opening 104 is connected to tubing sections 114 which are in turn connected to a fraction collector or other sample collection means (not shown). The tubing sections are preferably held in place on the base 54 by retaining brackets 116.

The well 90 is kept at a constant preselected temperature by heated water flowing from the heater 40 into an inlet passage 118 and into chamber retention manifold passage 120, as illustrated in FIG. 4. The heated water is then circulated within the walls of the chamber retention well through passages 122. The passages 122 are interconnected such that heated water flows through the passages 122 in a generally upward direction. Preferably, the wall of the chamber retention well 90 is made of aluminum or similar material with high thermal conductivity to facilitate heat transfer from the heated water to the water or gas contained within the well. The heated water flows from the passages 122 into the inlet 61 of the inlet manifold passage 62 of the heating and gassing block 38. The water then flows through the heating and gassing block 38 as was discussed previously.

An important feature of the apparatus of the present invention is the heating and gassing block that is used to heat and gas the nutrient solution at the same time in a small amount of space. The heating and gassing block provides a compact structure for gassing and efficient heat transfer.

Gassing a liquid cold and then heating the liquid, such as was done by some of the prior art methods, liberates gas that forms bubbles. This result is highly undesirable. It is believed that gassing the heated nutrient solution within the silicone tubing using the apparatus of the present invention eliminates formation of bubbles and eliminates adverse effects that bubbling may cause on the nutrient solution chemistry. In addition, heating and gassing the nutrient solution immediately prior to its use in the culture chamber eliminates the need for both overgassing and overheating to compensate for subsequent losses before entry into the culture chamber.

With the heating and gassing section being positioned directly before the culturing section, the nutrient solution contains sufficient gas so that the culturing chambers do not have to be directly gassed, as in the prior art. Consequently, the cells or microorganisms are not subjected to any bubbling action within the culturing chambers. Elimination of direct gassing and any resultant bubbling in the chamber is important when cells having a cell wall strength less than the surface tension of the nutrient solution are being cultured within the chamber. Many types of cells are destroyed by bubble surface tension, osmotic gradient across a bubble membrane boundry and mechanical agitation caused by bubble flow.

Although the present invention has been described with reference to preferred embodiments, workers skilled in the art will recognize that changes may be made in form and detail without departing from the spirit and scope of the invention.

What is claimed is:

1. An apparatus for growing and maintaining microorganisms or cells within a culturing device by delivering a nutrient solution through gas-diffusable tubing to the culturing device, the apparatus comprising:
    means for maintaining the culturing device within a fluid or gas bath at a predetermined temperature;
    a heating and gassing block having at least one tubing retaining groove in heat transfer relationship with a section of the tubing and having means for presenting gas to the tubing such that the gas diffuses through the tubing into the nutrient solution;
    means for pumping nutrient solution from a nutrient solution source through the tubing and into the culturing device; and
    a heating source having a single source of energy for delivery to both the bath and the heating and gassing block such that both the bath and the nutrient solution are maintained substantially at the predetermined temperature by delivery of energy from the single energy source.

2. The apparatus of claim 1 wherein the heating source is a water heater that is fluidly connected to both the heating and gassing block and to the means for maintaining the culturing device.

3. The apparatus of claim 2 wherein the means for maintaining the culturing device includes a plurality of water passages within a walled structure that defines a culturing chamber for maintaining the fluid or gas bath.

4. The apparatus of claim 3 wherein the heating and gassing block has a plurality of grooves in heat transfer relationship with sections of the tubing and has a plurality of water passages extending through the block and in fluid connection with the water passages of the means for maintaining the culturing device and with the heating source.

5. The apparatus of claim 4 wherein the block further includes a plurality of gas passages that are fluidly connectable to a gas source and which extend to an upper surface of the block and further including a cover having a lower surface disposed proximate the upper surface of the block for aiding diffusion of the gas into the tubing.

6. An improved apparatus used for the growth and maintenance of organisms within a culturing device by delivering a nutrient solution through gas-diffusable tubing to the culturing device, including a pump for pumping nutrient solution from a nutrient source through the tubing and into the culturing device, an energy source for providing energy, and a gas source for providing gas, the culturing device maintained in a well having a fluid or gas bath maintained at a predetermined temperature, the improvement comprising:
    a heating and gassing block having groove means for retaining a section of the tubing in heat transfer relationship with the heating and gassing block and means for presenting gas to the tubing such that the gas diffuses through the tubing into the nutrient solution, the heating and gassing block receiving energy from the energy source and gas from the gas source.

7. The apparatus of claim 6 wherein the groove means includes a plurality of grooves in heat transfer relationship with the tubing.

8. The apparatus of claim 6 wherein the energy source is a water heater that is fluidly connected to the well maintaining the culturing device and the heating and gassing block, and wherein the heating and gassing block has a plurality of water passages extending through the block in fluid connection with the water passages of the well.

9. The apparatus of claim 8 wherein the means for presenting gas includes a plurality of gas passages that are fluidly connectable to the gas source and which extend to an upper surface of the block and further including a cover having a lower surface disposed proximate the upper surface of the block aiding diffusion of the gas into the tubing.

10. The apparatus of claim 8 wherein the water from the water heater source is fluidly connected to flow first into the water passages of the well and then into the heating block and subsequently returning to the water heater.

11. An apparatus for growing and maintaining microorganisms or cells within a culturing device by delivering a nutrient solution through gas-diffusable tubing to the culturing device, the apparatus comprising:
    means for maintaining the culturing device within a fluid or gas bath at a predetermined temperature;
    a heating and gassing block having at least one tubing retaining groove in heat transfer relationship with a section of the tubing and having means for presenting gas to the tubing such that the gas diffuses through the tubing into the nutrient solution;
    means for pumping nutrient solution from a nutrient solution source through the tubing and into the culturing device; and
    a heating source having a source of energy for delivery to both the bath and the heating and gassing block.

12. The apparatus of claim 11 wherein the heating source is a water heater that is fluidly connected to both the heating and gassing block and to the means for maintaining the culturing device.

13. The apparatus of claim 12 wherein the means for maintaining the culturing device includes a plurality of water passages within a walled structure that defines a culturing chamber for maintaining the fluid or gas bath.

14. The apparatus of claim 13 wherein the heating and gassing block has a plurality of grooves in heat transfer relationship with sections of the tubing and has a plurality of water passages extending through the block and in fluid connection with the water passages of the means for maintaining the culturing device and with the heating source.

15. The apparatus of claim 14 wherein the block further includes a plurality of gas passages that are fluidly connectable to a gas source and which extend to an upper surface of the block and further including a cover having a lower surface disposed proximate the upper surface of the block for aiding diffusion of the gas into the tubing.

* * * * *